(12) United States Patent
Leyshon et al.

(10) Patent No.: US 11,261,142 B2
(45) Date of Patent: Mar. 1, 2022

(54) ISOBUTYLENE TO PROPYLENE PROCESS FLOW IMPROVEMENT

(71) Applicant: Lyondell Chemical Technology, L.P., Houston, TX (US)

(72) Inventors: David W. Leyshon, Houston, TX (US); Rick B. Watson, Houston, TX (US)

(73) Assignee: Lyondell Chemical Technology, L.P., Houston, TX (US)

( * ) Notice: Subject to any disclaimer, the term of this patent is extended or adjusted under 35 U.S.C. 154(b) by 0 days.

(21) Appl. No.: 17/360,824

(22) Filed: Jun. 28, 2021

(65) Prior Publication Data

US 2021/0403396 A1 Dec. 30, 2021

Related U.S. Application Data

(60) Provisional application No. 63/045,673, filed on Jun. 29, 2020.

(51) Int. Cl.
*C07C 5/27* (2006.01)
*B01J 23/44* (2006.01)
(Continued)

(52) U.S. Cl.
CPC .......... *C07C 5/2724* (2013.01); *B01D 3/143* (2013.01); *B01J 19/245* (2013.01); *B01J 21/04* (2013.01); *B01J 23/44* (2013.01); *C07C 5/13* (2013.01); *C07C 5/22* (2013.01); *C07C 5/23* (2013.01); *C07C 5/25* (2013.01); *C07C 5/27* (2013.01); *C07C 6/02* (2013.01); *C07C 6/04* (2013.01);
(Continued)

(58) Field of Classification Search
CPC .......... C07C 5/2724; C07C 5/23; C07C 5/27; C07C 5/22; C07C 5/25; C07C 5/13; C07C 6/02; C07C 7/09; C07C 7/04; C07C 6/04; C07C 7/005; C07C 5/02; C07C 5/05; C07C 5/03; C07C 2523/44; C07C 2521/04; B01J 19/245; B01J 23/44; B01J 21/04; B01J 2219/0004; B01D 3/143
See application file for complete search history.

(56) References Cited

U.S. PATENT DOCUMENTS 6,323,384 B1    11/2001   Powers et al.
6,872,862 B2 *   3/2005   Bridges ................ C07C 5/2568
                                                585/324
(Continued)

FOREIGN PATENT DOCUMENTS

FR          3081461 A1 *   11/2019              C07C 7/04

OTHER PUBLICATIONS

The International Search Report and Written Opinion for PCT/US2021/039419 dated Oct. 11, 2021.

*Primary Examiner* — Ali Z Fadhel (57) ABSTRACT

Improved systems and methods for producing propylene from olefins including isobutylene is disclosed. The improvements combine streams containing co-produced 1-butene, 2-butene, butadiene, and heavy olefins (C5+) exiting both a metathesis reactor and a skeletal isomerization reactor in a gasoline fractionation tower to remove the heavy olefins. The C4-containing distillate from the gasoline fractionation tower is then fed to a hydroisomerization unit to form mono-olefins and 2-butene. The resulting 2-butene rich stream can then be utilized in metathesis reactions to increase the production of propylene while increasing the lifetime of the metathesis catalyst.

19 Claims, 1 Drawing Sheet

(51) Int. Cl.
  *B01J 21/04*  (2006.01)
  *B01J 19/24*  (2006.01)
  *C07C 6/04*   (2006.01)
  *C07C 7/09*   (2006.01)
  *C07C 7/04*   (2006.01)
  *B01D 3/14*   (2006.01)
  *C07C 7/00*   (2006.01)
  *C07C 6/02*   (2006.01)
  *C07C 5/13*   (2006.01)
  *C07C 5/25*   (2006.01)
  *C07C 5/23*   (2006.01)
  *C07C 5/22*   (2006.01)
  *C07C 5/02*   (2006.01)
  *C07C 5/03*   (2006.01)
  *C07C 5/05*   (2006.01)

(52) U.S. Cl.
  CPC ............... *C07C 7/005* (2013.01); *C07C 7/04* (2013.01); *C07C 7/09* (2013.01); *B01J 2219/0004* (2013.01); *C07C 5/02* (2013.01); *C07C 5/03* (2013.01); *C07C 5/05* (2013.01); *C07C 2521/04* (2013.01); *C07C 2523/44* (2013.01)

(56) References Cited

U.S. PATENT DOCUMENTS

| | | | |
|---|---|---|---|
| 7,074,976 B2* | 7/2006 | Powers | C07C 6/04 585/324 |
| 2004/0267067 A1* | 12/2004 | Bridges | C07C 5/2568 585/324 |
| 2005/0043574 A1* | 2/2005 | Powers | C07C 6/04 585/324 |
| 2021/0198166 A1* | 7/2021 | Reich | C07C 4/06 |

* cited by examiner

ISOBUTYLENE TO PROPYLENE PROCESS FLOW IMPROVEMENT

PRIOR RELATED APPLICATIONS

This application claims the benefit of priority to U.S. Provisional Patent Application No. 63/045,673, filed on Jun. 29, 2020, which is incorporated herein by reference in its entirety.

FEDERALLY SPONSORED RESEARCH STATEMENT

Not applicable.

REFERENCE TO MICROFICHE APPENDIX

Not applicable.

FIELD OF THE DISCLOSURE

The disclosure relates to systems and methods of making propylene.

BACKGROUND OF THE DISCLOSURE

Propylene is one of the most versatile building blocks in the petrochemical industry in terms of its variety of end-use products and its multitude of production sources. It finds use as a base chemical for a wide variety of applications, including plastics, fuels, and functional derivatives such as acrylonitrile, propylene oxide, cumene/phenol, oxo alcohols, acrylic acid, isopropyl alcohol, oligomers, and other compounds. By far the most common use of propylene is the production of polypropylene. Polypropylene is the largest volume plastic in the world, greater than low-density, linear low-density, or high-density polyethylene individually. This polymer is mechanically rugged yet flexible, is heat resistant, and is resistant to many chemical solvents like bases and acids. This makes polypropylene ideal for various end-use industries, mainly in packaging and labeling, textiles, plastic parts and reusable containers of various types.

Conventionally, propylene is separated as a byproduct from petrochemical processes. The largest source of propylene is co-production from naphtha or liquefied petroleum gas in ethylene steam crackers; however, the quantity produced depends on the nature of feedstock. For heavier feedstocks with larger amounts of propane, butane, and naphtha, the quantity of propylene co-product is about 15%. If the feedstock is light, like ethane, then very little propylene (about 10 times less than naphtha) is produced. Even a 10% shift from naphtha to ethane can reduce available propylene production by about 7.5 million metric tons annually. Further, this source of propylene, especially in the United States, is diminishing as steam-cracker operators choose to crack ethane because it is an inexpensive component of shale gas.

The second largest amount of propylene (about 30%) comes from refineries as a byproduct from fluidized catalytic cracker (FCC) units that are operated for transportation fuel production. Recently, refiners have been able to increase propylene production in FCC's by optimizing catalyst and operating conditions. However, the potential for production of propylene in existing refinery FCC's is limited by the capacity of the units and the cost to debottleneck to accommodate increased volumes of gas.

Historically, ethylene steam crackers and FCC units have provided almost all of the petrochemical industry's propylene. However, over the past 15 years, the need for key propylene derivatives, such as polypropylene, has grown rapidly and quickly outpaced the need for ethylene derivatives. This increased demand has strained the propylene supply as propylene is still relegated to byproduct status from both steam crackers and FCC units. As a result, there exists a huge gap between market demand and supply of propylene in the world. To address this issue, the petrochemical industry has moved towards "on-purpose propylene" technologies to meet the demands.

Several on-purpose propylene technologies are available, with the most widely used technologies being propane dehydrogenation (PDH), olefin metathesis, and methanol to propylene (MTP). Unfortunately, some of these technologies have seen limited applicability. PDH, for instance, requires high investment. MTP requires high temperatures that lead to unfavorable propylene selectivity and coking of the active sites on the MTP catalysts.

In recent years, olefin metathesis has become an attractive option for on-purpose production of propylene. In a conventional olefin metathesis reaction, a 2-butene and an ethylene molecule are reacted to form two propylene molecules and other co-produced olefins dependent on the composition of the initial 2-butene and ethylene streams. Though the yield of propylene is much higher with olefin metathesis reactions than other on-purpose processes, the propylene/ethylene pricing spread is significant as it consumes valuable ethylene.

Advances have been made in the olefin metathesis process to improve propylene production and reduce cost. However, there still exists a need for the further development to produce larger amounts of propylene to meet global demand. Even incremental improvements in technology can mean the difference between a cost-effective propylene on-purpose production process, and cost prohibited energy and production losses.

SUMMARY OF THE DISCLOSURE

The present disclosure provides an improved system and method of producing propylene. The improvements increase the production of propylene by providing a flow path that allows for the conversion of isobutylene into a usable metathesis reactant without decreasing the lifetime of the metathesis catalyst.

In more detail, the presently disclosed metathesis system uses a skeletal isomerization reactor for isomerizing an isobutylene stream and a metathesis reactor. The improvements are directed to treatments of recycle streams in this metathesis system to form a 2-butene rich stream for the metathesis reaction. Streams with 1-butene, 2-butene, butadiene and heavy olefins (C5+) exiting both the metathesis and skeletal isomerization reactors are combined in a gasoline fractionation tower to remove the heavy olefins. The 1-butene, 2-butene, and butadiene remaining in the gasoline fractionation tower's distillate are then treated in a hydroisomerization hydrotreater to convert C4 diolefins (particularly butadiene) to mono-olefins and then 1-butene to 2-butene, forming a 2-butene rich stream that can be utilized as a recycle feed stream for the metathesis process.

In addition to providing a pathway for utilizing isobutylene in propylene production, the presently described system and methods are a more efficient recycling process for the streams exiting the metathesis and skeletal isomerization processes. The reduction of 1-butene in the metathesis recycle feed stream decreases the formation of heavy olefins that are eventually separated out and used as low value gasoline. As the heavy olefins cause coking in the metathesis reactor, a decrease in their formation increases the lifetime of metathesis catalyst by at least about 10%.

Further, the presently described system and methods result in an increase in propylene production (about 10% or more) when compared to metathesis systems that do not utilize an isobutylene isomerization process and/or a hydroisomerization hydrotreater. The use of both of these processes together results in a greater amount of 2-butene being made from a given isobutylene feed, which then increases the amount of propylene generated by the metathesis reaction.

The present methods and systems include any of the following embodiments in any combination(s) of one or more thereof:

A method of producing propylene comprising combining a C4+ olefin product stream from a skeletal isomerization unit and a C4+ olefin product stream from a metathesis unit. This combined stream is then introduced into a gasoline fractionation tower to separate the C5+ olefins from the C4 olefins to form a C5+ olefin stream and a gasoline fractionation distillate. The gasoline fractionation distillate is transferred to a hydroisomerization hydrotreater reactor to convert C4 diolefins in the gasoline fractionation distillate to C4 mono-olefins then convert 1-butene in the gasoline fractionation distillate to 2-butene. These conversions form a 2-butene-rich olefin product stream. The 2-butene-rich olefin product stream is then de-oxygenated to form a treated 2-butene rich stream that is co-fed with at least one ethylene stream into the metathesis unit to form propylene.

A method of producing propylene comprising producing a C4+ olefin product stream in a skeletal isomerization unit by isomerizing an isobutylene feed stream in a skeletal isomerization reactor and separating, in a butene distillation column, the isomerized feed stream into a C2-C3 olefin vapor stream, a recycle stream comprising isobutylene and a first portion of 1-butene, and the first C4+ olefin stream. A second C4+ olefin product stream is produced by a metathesis reactor unit. In the metathesis reactor unit, at least one ethylene stream is reacted with a 2-butene rich stream to form a metathesis product stream comprising C2+ olefins. The ethylene (C2) is separated out from this stream using a de-ethanizer unit, and produced propylene (C3) is separated out using a de-propanizer unit. A C4+ stream exits from the bottom of the de-propanizer unit. The C4+ olefin product stream from the skeletal isomerization unit and the C4+ olefin product stream from the metathesis unit are then combined in a hydroisomerization unit, wherein the combined streams are first separated in a gasoline fractionation tower to form a C5+ olefin stream and a C4 olefin distillate. The C4 olefin distillate is then introduced into a hydroisomerization hydrotreatment reactor that converts diolefins in the C4 olefin distillate to mono-olefins, then converts 1-butene in the C4 olefin distillate to 2-butene to form the 2-butene rich stream. This 2-butene rich stream is then fed into the metathesis reactor to produce propylene. In some embodiments, the C2-C3 olefin vapor stream from the skeletal isomerization unit is combined with the metathesis product stream such that the C2 and C3 from the skeletal isomerization unit can be recovered by the de-ethanizer and de-propanizer, respectively. In an alternative embodiment, the C2-C3 olefin vapor stream from the skeletal isomerization unit can be recycled into the skeletal isomerization reactor.

Any of the above methods, wherein the C4+ olefin product streams comprise 1-butene, 2-butene, butadiene, and C5+ diolefins and mono-olefins.

Any of the above methods, wherein at least 80% of the 1-butene is converted to 2-butene in the hydroisomerization hydrotreatment reactor.

Any of the above methods, wherein the hydroisomerization hydrotreater reactor contains Pd, Pt, Ru or Cu on silica, alumina or silica alumina as a catalyst. In some embodiments, the catalyst in the hydroisomerization hydrotreater reactor is palladium on an alumina support.

Any of the above methods, wherein the yield of propylene is at least 10% greater than the yield for methods that do not combine C4+ olefin product streams from a skeletal isomerization unit and a metathesis unit, separate out C5+ olefins from this combined stream, and then isomerize the remaining C4 olefins in a hydroisomerization hydrotreater to form a 2-butene rich stream for use in the metathesis reactor.

Any of the above methods, wherein the lifetime of the catalyst in the metathesis unit is 10% or more than the lifetime for methods that do not combine C4+ olefin product streams from a skeletal isomerization unit and a metathesis unit, separate out C5+ olefins from this combined stream, and then isomerize the remaining C4 olefins in a hydroisomerization hydrotreater to form a 2-butene rich stream for use in the metathesis reactor.

Any of the above methods, wherein the 2-butene rich stream is treated to remove oxygen-containing compounds before being fed into the metathesis reactor.

Any of the above methods, wherein the C5+ olefin stream is transferred to a refinery for gasoline blending.

A system for producing propylene comprising a skeletal isomerization unit, a metathesis unit, and a hydroisomerization unit. The skeletal isomerization unit has a skeletal isomerization reactor with an inlet for receiving at least an isobutylene feed stream and an outlet for release of a skeletal isomerization reactor stream; and, a butene distillation column fluidly connected to the outlet of the skeletal isomerization reactor, wherein the butene distillation column has a first outlet for release of a C2-C3 olefin vapor stream, a second outlet for release of a recycle stream comprising isobutylene and a first portion of 1-butene, and a third outlet for release of a skeletal isomerization product stream comprising 2-butene, a second portion of 1-butene, butadiene and C5+ olefins, wherein the recycle stream is introduced into the skeletal isomerization reactor at the inlet. The metathesis unit has a metathesis reactor with a first inlet for receiving at least an ethylene feed stream, a second inlet for receiving a C4 olefin feed stream, and outlet for releasing a metathesis product stream; a de-ethanizer unit with an inlet fluidly connected to the metathesis reactor for receiving the metathesis product stream, wherein the de-ethanizer has a top outlet for a recycle ethylene stream that can be combined with the ethylene feed stream and a bottom outlet for release of a de-ethanized stream; and, a de-propanizer unit with an inlet fluidly connected to the de-ethanizer unit for receiving the de-ethanized stream, wherein the de-propanizer has a top outlet for a produced propylene stream and a bottom outlet for release of an untreated metathesis stream comprising C4+ hydrocarbons. The hydroisomerization unit has a gasoline fractionation tower with an inlet for receiving and combining the untreated metathesis stream and the skeletal isomerization product stream, wherein the gasoline distillation tower separates the combined streams into a C5+ stream and a C4 stream; a hydroisomerization reactor with an inlet for receiving the C4 stream from the gasoline fractionation tower, and an outlet for a 2-butene rich C4 olefin stream, wherein the hydroisomerization reactor converts diolefins to mono-olefins and isomerizes 1-butene to 2-butene; a first line exiting the bottom of the gasoline fractionation tower for carrying the C5+ stream to a refinery for gasoline blending; a second line exiting the top of the hydroisomerization reactor for carrying the 2-butene rich C4 olefin stream to a de-oxygenation unit; and a third line exiting the de-oxygenation unit for carrying the de-oxygenated 2-butene rich C4 olefin stream to the second inlet of the metathesis reactor.

The above system can further comprise a line fluidly connecting the first outlet of the butene distillation column to the inlet of the de-ethanizer such that the C2-C3 olefin vapor stream undergoes separation in the de-ethanizer and the de-propanizer.

The above system can further comprise a recycle line for carrying the C2-C3 olefin vapor stream to the skeletal isomerization reactor.

Any of the above systems, wherein the de-oxygenation unit removes water, oxygen, and oxygenates from the 2-butene rich C4 olefin stream.

Any of the above systems, wherein the hydroisomerization reactor has a catalyst having one or more of Pd, Pt, Ru, Cu on a silica, alumina or silica/alumina support.

Any of the above systems, wherein the catalyst in the hydroisomerization reactor unit is palladium on an alumina support.

Although the systems and methods are described for use with conventional metathesis reactions, they can be broadly applicable to other reactions that utilize a 2-butene rich feed, including autometathesis.

This summary is provided to introduce a selection of concepts that are further described below in the detailed description. This summary is not intended to identify key or essential features of the claimed subject matter, nor is it intended to be used as an aid in limiting the scope of the claimed subject matter.

BRIEF DESCRIPTION OF THE DRAWINGS

The FIGURE provides a metathesis system according to one embodiment of the disclosure.

Definitions

Figure 1:
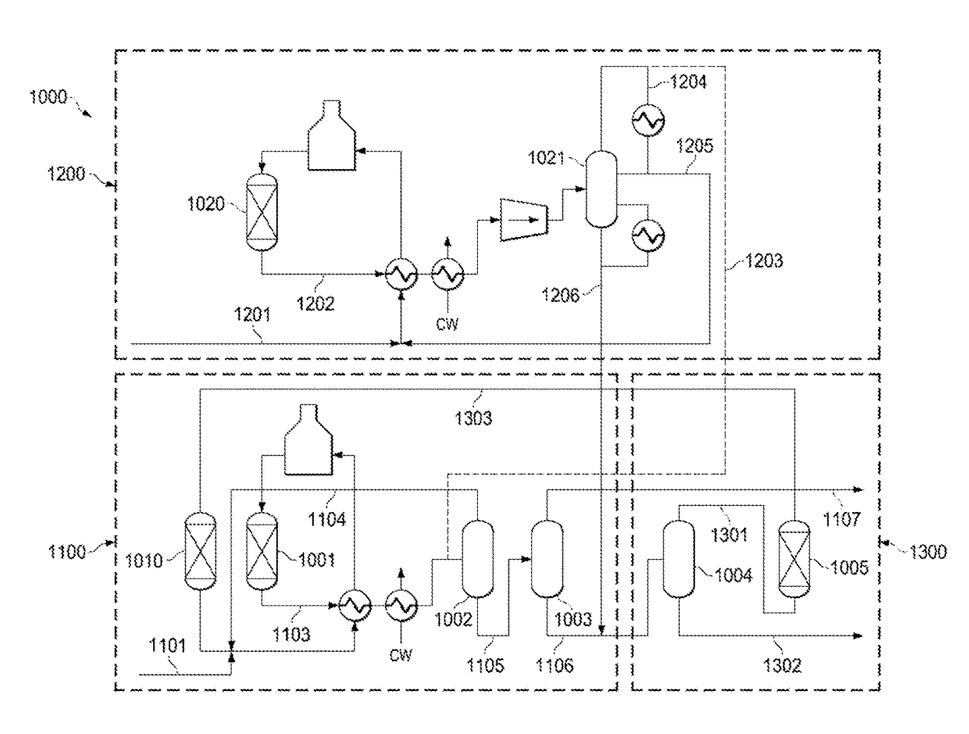

As used herein, the term "metathesis" refers to the reaction of two olefins to produce propylene. In "conventional metathesis", the metathesis reaction proceeds with 2-butene and ethylene to produce propylene. Depending on the source of the 2-butene feed, it may also include various C4+ fractions, some of which react with each other or ethylene to produce non-propylene products. The presence and amounts of these other reaction products is dependent on the composition of the C4 feed. In contrast, the term "autometathesis" refers to a metathesis reaction that proceeds with only a C4 hydrocarbon feed stream reacting in the absence of ethylene as a feed. For each of these metathesis reactions, optional recycle streams containing reaction products, or unreacted reactants, can undergo further reactions with the feed(s) in the metathesis reactor.

As used herein, the term "skeletal isomerization" refers to an isomerization process that involves the movement of a carbon atom to a new location on the skeleton of the molecule, e.g., from a branched isobutylene skeleton to a linear or straight chain (not branched) butene skeleton. In contrast, "double bond isomerization" involves the movement of a double bond within the existing skeleton while the carbon atoms that form the carbon atom skeleton remain in their original locations in that skeleton.

In the presently disclosed system, the double bond isomerization is "hydroisomerization", which reacts olefins such as 1-butene and small quantities of hydrogen over noble metal catalysts (such as Pt or Pd) or supported metal catalyst. The thermodynamic equilibrium favors formation of interior olefins at lower temperatures, thus the hydroisomerization in the present disclosure occurs at moderate temperatures. Due to the reaction conditions and catalysts, hydrogenation reactions also occur with the hydroisomerization, allowing for the conversion of C4 diolefins to mono-olefins before the conversion of exterior olefins to interior olefins.

As used herein, the term "raffinate" refers to a residual stream of olefins obtained after the desired chemicals/material have been removed. In the cracking/crude oil refining process, a butene or "C4" raffinate stream refers to the mixed 4-carbon olefin stream recovered from the cracker/fluid catalytic cracking unit. The term "Raffinate 1" refers to a C4 residual olefin stream obtained after separation of butadiene (BD) from the initial C4 raffinate stream. "Raffinate 2" refers to the C4 residual olefin stream obtained after separation of both BD and isobutylene from the initial C4 raffinate stream. "Raffinate 3" refers to the C4 residual olefin stream obtained after separation of BD, isobutylene, and 1-butene from the initial C4 raffinate stream. In some embodiments of the present disclosure, the isobutylene separated from Raffinate 1 can be used as a source for the skeletal isomerization process, especially when C4 alkanes have first been removed.

The term "distillation tower" refers to a tower that is capable of separating a liquid mixture into its component parts or fractions by selective boiling and condensation. In a typical distillation, a liquid mixture is heated in the tower wherein the resulting vapor rises up the tower. The vapor condenses on trays inside the tower, and returns to the bottom of the tower, refluxing the rising distillate vapor. The more reflux and/or more trays provided, the better the tower's separation of lower boiling materials from higher boiling materials. Sometimes, a packing material is used in the towers (instead of trays) to improve contact between the two phases.

The effluent exiting the top of a distillation tower is called the "overhead product". If the overhead product is in the form of a vapor it is referred to herein as a "vapor"; alternatively, overhead products in the form of a liquid are referred to herein as a "distillate" or "liquid distillate". The distillate can be used for reflux back to the distillation tower.

The terms "fractionator", "gasoline fractionation tower", and "gasoline fractionator" are used interchangeably to refer to a distillation tower that separates heavier fractions of hydrocarbons (C5+) from lighter fractions of hydrocarbons.

The term "trays" in reference to distillation towers denotes theoretical equilibrium stages inside a distillation tower.

A plus sign (+) is used herein to denote a composition of hydrocarbons with the specified number of carbon atoms plus all heavier components. As an example, a C4+ stream comprises hydrocarbons with 4 carbon atoms plus hydrocarbons having 5 or more carbon atoms.

The term "heavy olefins" is used to denote compositions of C5+ hydrocarbons, including mono-olefins and diolefins.

The term "2-butene" as used herein refers to both cis-2-butene and trans-2-butene.

The term "de-oxygenating" as used herein refers to the removal of oxygen-containing compounds, including by not limited to, water, oxygen (O2), and oxygenates such as acetone, dimethyl ether, methanol, t-butyl alcohol.

The use of the phrase "substantially pure" means a level of purity that is at least 95%.

The term "conversion" is used to denote the percentage of a component fed which disappears across a reactor.

The use of the word "a" or "an" when used in conjunction with the term "comprising" in the claims or the specification means one or more than one, unless the context dictates otherwise.

The term "about" means the stated value plus or minus the margin of error of measurement or plus or minus 10% if no method of measurement is indicated.

The use of the term "or" in the claims is used to mean "and/or" unless explicitly indicated to refer to alternatives only or if the alternatives are mutually exclusive.

The terms "comprise", "have", "include" and "contain" (and their variants) are open-ended linking verbs and allow the addition of other elements when used in a claim.

The phrase "consisting of" is closed, and excludes all additional elements.

The phrase "consisting essentially of" excludes additional material elements, but allows the inclusions of non-material elements that do not substantially change the nature of the invention.

The following abbreviations are used herein:

| ABBREVIATION | TERM |
| --- | --- |
| BD | butadiene |
| FCC | fluidized catalytic cracker |
| MTBE | methyl-t-butyl ether |
| MTP | Methanol to propylene |
| PDH | propane dehydrogenation |
| PO/TBA | propylene oxide/t-butyl alcohol |
| WHSV | Weight hourly space velocity |

DESCRIPTION OF EMBODIMENTS OF THE DISCLOSURE

The present disclosure provides an improved system and methods of producing propylene, wherein the improvements combine and treat reaction product streams from a metathesis and a skeletal isomerization reactor such that isobutylene is now used in the formation of propylene. Specifically, co-produced 1-butene, 2-butene, butadiene, and heavy olefins (C5+) exiting both reactors are combined in a gasoline fractionation tower to remove the heavy olefins as a gasoline product. The lighter C4 olefins are then treated in a hydroisomerization unit to first convert C4 diolefins to mono-olefins, and then convert 1-butene to 2-butene to form a 2-butene rich recycle stream that can be utilized as a recycle feed for the metathesis reactor.

Without the diolefins and with a reduced amount of 1-butene in the metathesis recycle feed, the metathesis catalyst will experience a decrease in coking and have an increase in lifetime. Further, at least 10% more propylene can be formed from the 2-butene rich metathesis feed than metathesis systems without these changes to the process flow of the product streams from the metathesis and skeletal isomerization reactor.

This improved system and method also provide an additional use for isobutylene that is produced during cracking. Isobutylene is separated from C4 raffinate streams derived from the cracker/fluid catalytic cracking process and used to form methyl tertiary-butyl ether (MTBE). Other than MTBE production, there have been limited uses for isobutylene. Should MTBE demand decrease, on-site stores of unused isobutylene would increase. The present disclosure provides another use of isobutylene that will also help meet the global demand for propylene.

On-purpose propylene production via metathesis is particularly attractive because it allows for conversion of C2 and C4 olefins to polymer grade propylene. In conventional metathesis methods for producing propylene, the C2 and/or C4 feedstocks are reacted with a metathesis catalyst in the gas phase at high temperatures (e.g. about 300-800° F. for W-based catalyst). This higher temperature reaction is unfavorable for the thermodynamic equilibrium-controlled propylene selectivity as larger amounts of 1-butene and diolefins are co-produced. These co-produced C4 diolefins are then recycled back to the metathesis reactor where, at the high metathesis temperatures, these undesirable olefins produce coke that limits the metathesis catalyst lifetime. Further, the co-produced 1-butene mono-olefins and C4 diolefins react with valuable C2 and 2-butene to produce little, if any, additional propylene.

To enhance propylene yield and catalyst lifetime, process flows for the various co-produced olefin streams have been modified to treat these streams, with the objective of producing a recycle stream suitable for the high temperature environment with limited coking. U.S. Pat. Nos. 6,872,862 and 7,074,976 are two such process flow designs.

U.S. Pat. No. 7,074,976 describes a system that performs double bond isomerization and selective hydrogenation on an incoming C4 stream to convert diolefins to mono-olefins and some 1-butene to 2-butene, wherein this treated stream is then sent to the metathesis reactor. The C5+ metathesis reaction co-products are sent directly to a skeletal isomerization reactor, which converts isobutylene to linear butenes without affecting the remaining co-produced olefins. The stream exiting the skeletal isomerization reactor is then sent to the double bond isomerization and selective hydrogenation unit, where the 1-butene is expected to isomerize to 2-butene, before being recycled to the metathesis unit for further reaction. However, this isomerization of 1-butene to 2-butene will not happen to an appreciable extent due to the presence of the C5+ compounds, particularly the C5+ diolefins. Though this recycle stream is an improvement, the co-produced heavy C5+ olefins, diolefins and 1-butene are still being recycled to the metathesis unit and produce coke without appreciable amounts of propylene produced.

U.S. Pat. No. 6,872,862 describes a similar system but adds a distillation tower before the metathesis reactor to separate 1-butene and isobutylene from the metathesis feed. The 1-butene and isobutylene separated out from this feed are sent to a skeletal isomerization reactor to form linear olefins that then undergo double bond isomerization reactions before being recycled back to the distillation tower. The heavy olefins produced in the skeletal isomerization reactor are sent to the double bond isomerization unit, reducing the ability to convert 1-butene to 2-butene. The heavy olefins then pass through the new distillation tower and enter the metathesis unit where they will produce coke. As with U.S. Pat. No. 7,074,976, there are some improvements to the recycle feed. However, there is still an increase in diolefins and heavy olefins in the metathesis unit feed, which will reduce the metathesis catalyst run length. Further, this method relies on a large and costly distillation tower that has to handle the heavier (C5+) olefins in addition to the C2-C4 olefins, thus increasing the overall cost of the system.

Both U.S. Pat. Nos. 7,074,976 and 6,872,862 have a reduced ability to isomerize 1-butene to 2-butene due to the presence of heavy olefins in the isomerization units. This results in less propylene being made while even more heavy olefins are being produced and allowed to coke the metathesis catalyst.

The present system and methods overcome the issues in the conventional metathesis process design, including the designs in U.S. Pat. Nos. 6,872,862 and 7,074,976, by a unique modification to the flow process such that C4 streams exiting both the skeletal isomerization reactor and the metathesis reactor are combined, distilled by a gasoline fractionation tower to remove C5+ heavy mono- and diolefins, and then treated to remove or reduce problematic co-produced C4 diolefins and 1-butene. Specifically, the gasoline fractionation tower's distillate is hydrotreated to convert C4 diolefins to mono-olefins and convert terminal olefins such as 1-butene to internal olefins such as 2-butene. The remaining 2-butene rich stream can then be recycled to the metathesis reactor. By treating both C4 streams together, this new process flow prevents diolefins from being recycled back to the metathesis reactors, reducing coking on the metathesis catalyst. Further, this improved process flow increases the amount of 2-butene in the recycle stream compared to a system that only combines the C4 streams exiting both the skeletal isomerization reactor and the metathesis reactor without a hydrotreatment process. The use of both an isobutylene isomerization process and a hydroisomerization hydrotreater increases the amount of 2-butene for a given initial amount of isobutylene. This results in an even greater amount of propylene production compared to systems without the present modifications to the flow process.

The FIGURE displays one embodiment 1000 of an improved metathesis system for use with the presently disclosed methods. This system is utilized for the examples described below and is designed to convert isobutylene and non-preferred metathesis reaction products into a 2-butene rich stream for recycling to the metathesis reactor for further propylene production. However, this embodiment is exemplary only, and the 2-butene rich stream can be broadly applied to other processes that utilize 2-butene in their reactions, including conventional metathesis and autometathesis.

In more detail, the system 1000 in the FIGURE has a convention metathesis process 1100, a skeletal isomerization process 1200, and a hydroisomerization process 1300 according to the presently disclosed methods. As the hydroisomerization process 1300 combines the C4 components of streams (1106/1206) from both the metathesis and skeletal isomerization processes, these processes will be discussed first.

For embodiment 1000, the conventional metathesis process 1100 has an ethylene feed 1101, a metathesis reactor unit 1001, a de-ethanizer tower 1002, and a de-propanizer tower 1003. The metathesis reactor 1001 also has inlets for receiving an ethylene recycle stream from the de-ethanizer tower 1002, and a 2-butene rich recycle stream 1303 from hydroisomerization process 1300. This 2-butene rich recycle stream is the butene source for the conventional metathesis reaction. The system 1000 is a steady state system. Following any downtime in the metathesis process, the olefin metathesis will rely on a stored 2-butene rich stream for the startup of the metathesis reaction.

The ethylene feed 1101 enters the metathesis reactor 1001, where it reacts with the recycled 2-butene stream over a heterogeneous supported metathesis catalyst to form a reaction product mixture comprising C2+ hydrocarbons, in addition to unreacted ethylene and 2-butene.

Olefin metathesis is a high temperature and high pressure reaction, although the operating conditions can vary widely. The temperature range for the metathesis reactor 1001 is between about 300° F. to about 800° F. Alternatively, the temperature for the metathesis reactor 1001 is between about 300° F. to about 700° F., about 300° F. to about 500° F., about 500° F. to about 800° F., or about 400° F. to about 700° F. In yet another alternative, the temperature is about 600° F. The pressure conditions are from about 200 to about 600 psig. Alternatively, the pressure for the metathesis reaction is between about 200 psig to about 450 psig, 350 psig to about 600 psig, or 400 psig to about 450 psig. In yet another alternative, the pressure is about 450 psig.

The metathesis reactor 1001 is operated with a fixed bed catalyst that includes oxides of Group II, VIB and Group VIIB metals such as MgO, $WO_3$, $MoO_3$, and $Re_2O_3$. Alternatively, the catalyst is W- or Mg-based. Any fixed bed catalyst support material can be used, including inorganic oxides such as silica, alumina, zirconia, and zeolites. In some embodiments, the catalyst is mixture of a W-based material with MgO, which increases the activity of the W-based material by a factor of about 3 to 4. Alternatively, the catalyst is $WO_3$ supported on $SiO_2$, with or without MgO particles in the same fixed bed to activate the $WO_3$.

Some metathesis reactors include isomerization catalysts as a topping bed at the inlet of the metathesis reactor so that an isomerization reaction of 1-butene to 2-butene occurs within the reactor before any metathesis reactions. The present system does not include such an isomerization catalyst arrangement because the high reactor temperatures lead to an isomerization of 2-butene to 1-butene, which reduces propylene formation. However, some metathesis catalysts that can be used in the presently described system may contain some MgO, which is an isomerization catalyst. The amount of MgO is kept low enough in metathesis catalysts such as $WO_3$ supported on $SiO_2$ to prevent isomerization of 2-butene to 1-butene, but high enough to increase the activity of the metathesis catalyst and subsequent increase in propylene production.

The ethylene feed flow rate, and the recycle stream(s) flow rate, over the fixed bed catalyst is from about 1 to 25 weight hourly space velocity (WHSV), depending on the feeds' composition. In some embodiments, the WHSV for the recycle streams is about 15. Alternatively, the WHSV is chosen such that there are one to two moles of ethylene feed for every mole of the C4 feed.

As mentioned above, the higher temperature metathesis reaction is unfavorable for the thermodynamic equilibrium-controlled propylene selectivity. Thus, the resulting metathesis reaction product effluent is a mixed C2-C5+ hydrocarbon stream 1103 that can then be separated according to carbon number groups by technology known in the art. In system 1000, the metathesis process 1100 has a series of two distillation towers, wherein the first tower 1002 is a de-ethanizer for removal of ethylene overhead and the second tower 1003 is a de-propanizer where propylene is removed overhead.

In the first distillation tower 1002, the ethylene that was not consumed or was generated during the metathesis is separated from the larger hydrocarbons and removed from the top of the de-ethanizer tower 1002 and returned to the metathesis reactor 1001 as recycle stream 1104. The C3+ stream 1105 exits the first distillation tower 1002 from the bottom and is sent to a second distillation tower 1003, wherein C3 is removed from the top of the tower 1003 as a substantially pure, reagent grade propylene stream 1107. Though not shown in the FIGURE, the metathesis process can also include a storage unit for storing the produced propylene exiting the de-propanizer 1003.

Like the metathesis reactor 1001, the operating conditions for the de-ethanizer 1002 and de-propanizer 1003 can vary. In some embodiments, the de-ethanizer 1002 has about 20 to 40 trays, or stages of separation. Alternatively, the de-ethanizer 1002 has about 20 to 35 trays, 25 to 40 trays, or about 30 trays. The operating pressure is between about 300 and 500 psig, or between about 350 and 450 psig, or about 400 psig. The operating temperature is between about −10 and about 200° F. In some embodiments, the temperature at the bottom of de-ethanizer 1002 is about 180° F. and the temperature at the top of the de-ethanizer is about −1° F.

The de-propanizer 1003 is slightly larger than the de-ethanizer. In some embodiments, the de-propanizer 1003 has about 30 to 50 trays. Alternatively, the de-propanizer 1003 has about 30 to 45 trays, 35 to 50 trays, or about 40 trays. The operating pressure is between about 150 and 350 psig, or between about 200 and 300 psig, or about 260 psig. The operating temperature of the de-propanizer is higher than that of the de-ethanizer, and is between about 100 and about 250° F. In some embodiments, the temperature at the bottom of de-propanizer 1002 is about 200° F. and the temperature at the top of the de-propanizer is about 110° F.

After the C3 is removed, the higher carbon number olefins (C4+) exit the bottom of the de-propanizer 1003. In previous metathesis systems, this C4+ stream 1106 is recycled back to the metathesis reactor, wherein the heavy olefins and diolefins produce coke that decreases the lifetime of the metathesis catalyst and little, if any, propylene. In the presently disclosed system, the C4+ stream 1106 is sent to a gasoline fractionation tower 1004 and a hydrotreater 1005 to undergo further treatment as will be described below for the hydroisomerization process 1300.

The presently described system 1000 utilizes a skeletal isomerization process 1200 alongside the metathesis reactor process 1100 to isomerize isobutylene to linear butenes. The skeletal isomerization process 1200 has a skeletal isomerization reactor 1020 and a butene distillation tower 1021.

Unlike conventional metathesis systems such as those described in U.S. Pat. Nos. 6,872,862 and 7,074,976, the skeletal isomerization process 1200 is not operated in-line with the metathesis process 1100. Rather, it runs separately in the presently disclosed system. The skeletal isomerization of isobutylene is equilibrium controlled, which means the product stream will contain unreacted isobutylene. By running the system separately, this unreacted isobutylene can be returned to the skeletal isomerization reactor 1020 repeatedly until it is isomerized instead of being introduced into the metathesis reactor.

In more detail, a skeletal isomerization reactor 1020 receives an isobutylene feed 1201 for isomerization into a linear C4 olefin mixture that has less than 40% of C5+ olefins and diolefins. The isobutylene can be from any source. In some embodiments, the isobutylene comes from a Raffinate 1 stream derived from a cracker/fluid catalytic cracking unit and has had its C4 alkanes removed. Alternatively, the isobutylene can come from a stream derived from a propylene oxide/t-butyl alcohol (PO/TBA) plant. The dehydration of the t-butyl alcohol can result in a more purified isobutylene stream than a stream sourced from a cracker.

Though FIGURE displays the skeletal isomerization reactor 1020 as one reactor, it can be any number of reactors. In some embodiments, there are three or more reactors in parallel. This allows for first reactor to be started and placed online, and then a second reactor can be placed online sometime later, resulting in two reactors running parallel. When the first reactor needs to be regenerated and taken offline, the third reactor can be placed online. This process can be repeated such that at least two reactors are running in parallel at all times, and the regeneration process can be staggered. The same offline/online pattern can be scaled up for systems with more than three skeletal isomerization reactors.

The operating conditions for the skeletal isomerization reactor 1020 can vary widely. The temperature range for the skeletal isomerization reactor 1020 is between about 500° F. to about 900° F. Alternatively, the temperature for the skeletal isomerization reactor 1020 is between about 500° F. to about 800° F., 600° F. to about 900° F., or 600° F. to about 700° F. In yet another alternative, the temperature is about 700° F. or about 750° F. The pressure conditions are from about 5 to about 20 psig. Alternatively, the pressure for the skeletal isomerization is between about 5 psig to about 12 psig, 8 psig to about 20 psig, or 8 psig to about 140 psig. In yet another alternative, the pressure is about 10 psig.

The skeletal isomerization reactor 1020 is operated with a fixed bed catalyst and a feed flow rate of about 1 to 20 weight hourly space velocity (WHSV) or about 2 WHSV. The fixed bed catalyst can include any skeletal isomerization catalyst such as zeolites. In some embodiments, the catalyst is ferrierite or Zeolite Socony Mobil-35.

As mentioned above, the isobutylene is not completely consumed during the isomerization reaction. Thus, the olefin stream 1202 exiting the skeletal isomerization reactor 1020 is separated according to normal boiling points by technology known in the art. In the FIGURE, the skeletal isomerization process 1200 utilizes a butene distillation tower 1021 to separate the olefins exiting the skeletal isomerization reactor 1020. The operating conditions for the butene distillation tower 1021 vary. The butene distillation tower 1021 has about 30 to 70 trays. Alternatively, the butene distillation tower 1021 has about 30 to 50 trays, about 50 to 70 trays, about 40 to 60 trays, or about 50 trays. The operating pressure is between about 75 and 500 psig, or between about 100 and 130 psig, or about 115 psig. In some embodiments, the butene distillation tower 1021 has an operating temperature between 100 and 300° F., with the temperature fluctuating across the height of the tower. In some embodiments, the temperature of butene distillation tower 1021 is about 280° F. at the bottom of the tower and about 135° F. at the top of the tower.

Three streams exit the butene distillation tower 1021: a top vapor stream 1203/1204, a bottom stream 1206, and a liquid distillate stream 1205. The liquid distillate stream 1205 is mostly un-reacted isobutylene and 1-butene due to 1-butene boiling less than one degree higher than isobutylene. This stream 1205 can be fed back to the skeletal isomerization reactor to increase the conversion of isobutylene to linear butenes. As recovery of isobutylene for recycling back to the skeletal isomerization reactor is paramount, about 50% of the produced 1-butene in stream 1202 is expected to also be recycled back to the skeletal isomerization reactor in stream 1205.

During the skeletal isomerization reaction, some C2-C3 are produced, especially when the isomerization catalyst is freshly regenerated. As these compounds cannot be condensed in a butene distillation tower, a C2-C3 vapor stream exits the top of the tower 1021. This stream can be combined with distillate stream 1205 via pathway 1204 and recycled back to the skeletal isomerization reactor to shift the equilibrium of the reaction inside the skeletal isomerization reactor. Alternatively, this stream can be combined with the reaction products 1103 exiting the metathesis reactor 1001 via pathway 1203 to facilitate the recovery of the C2 and C3, separately, and further increase the amount of recovered propylene. In yet another alternative, this stream can be sent to a de-propanizer (not shown) to recover the C3, with the remaining components being recycled back to the skeletal isomerization reactor. In a variation, this de-propanizer can recover C3 from stream 1202 before it enters the butene tower 1021.

A C4+ product stream 1206 exits the bottom of the butene distillation tower 1021.

The presently described system improves upon conventional metathesis systems by utilizing new flow pathways and treatment methods for C4+ product streams exiting the olefin metathesis and skeletal isomerization reactors. As shown in the hydroisomerization process 1300, the C4+ stream 1206 exiting the butene distillation tower is combined with the C4+ stream 1106 from the metathesis reaction. This allows for the C4 components of both streams to be treated simultaneously by the hydroisomerization process 1300 before being recycled to the metathesis reactor 1001 for further propylene production.

In the hydroisomerization process 1300, the combined streams 1106/1206 are first introduced into a gasoline fractionation tower unit 1004 and separated according to normal boiling points. Because the gasoline distillation tower 1004 is only separating co-produced C4+ olefins, it is smaller than towers 1002, 1003, and 1021. In some embodiments, the gasoline distillation tower 1004 has about 10 to 30 trays. Alternatively, the gasoline distillation tower 1004 has about 10 to 25 trays, 15 to 30 trays, or about 20 trays. The operating pressure is between about 100 and 200 psig, or between about 110 and 150 psig, or about 115 psig.

Heavy olefins (C5+) are removed from the bottom of gasoline distillation tower 1004 via pathway 1302. These heavy olefins can be used in other processes, sold as a gasoline blending component, or undergo further treatment to improve its quality and/or value. In some embodiments, pathway 1302 can be a pathway for carrying the heavy olefins to a refinery for gasoline blending.

The distillate stream 1301 from the top of the gasoline distillation tower 1004 is fed to a hydroisomerization hydrotreater unit 1005 which converts any diolefins present to mono-olefins before converting 1-butene to 2-butene. The operating conditions of the hydroisomerization hydrotreater unit 1005 are such that all of the diolefins must be converted to mono-olefins before any 1-butene (or other terminal olefins) can be converted to 2-butene (or other internal olefins). This adjustment allows for the removal of one class of components (diolefins) known to produce coke in the metathesis reactor.

The hydroisomerization of 1-butene to 2-butene is controlled by equilibrium and is temperature dependent. The temperature range for the hydrotreater unit is between about 100° F. to about 250° F., which is much lower than the metathesis reactor, and favors the isomerization of 1-butene to 2-butene. Alternatively, the temperature for the hydrotreater unit 1005 is between about 100° F. to about 200° F., about 120° F. to about 250° F., about 150° F. to about 200° F., about 140° F. to about 220° F., or about 180° F. to about 220° F. In yet another alternative, the temperature is about 160° F. In these temperature ranges, the conversion of 1-butene to 2-butene is greater than 80%. In some embodiments, the conversion is about 90% or higher.

The pressure conditions for the hydrotreater unit 1005 are from about 50 to about 600 psig. Alternatively, the pressure for the hydrotreater unit 1005 is between about 80 psig to about 450 psig, 350 psig to about 600 psig, or 400 psig to about 450 psig. In yet another alternative, the pressure is about 425 psig.

Any hydroisomerization catalyst can be used in the hydrotreater unit 1005, including metals from Group 10 on supported catalyst such as Pd on alumina, oxides of Group II, VIB and Group VII B metals such as aluminum oxide, and acidized clay catalysts.

A 2-butene rich stream 1303 is removed from the effluent of the hydroisomerization hydrotreater reactor 1005 for recycling to the metathesis reactor 1001. The metathesis reactor is sensitive to oxygen and oxygenates, thus stream 1303 is first sent to a dryer unit 1010 to dry and remove water, oxygen and oxygenates (such as acetone, dimethyl ether, methanol, t-butyl alcohol and the like) from stream 1303. This treated stream is then recycled to the metathesis reactor 1001. Once it is introduced into the metathesis reactor, the 2-butene reacts with the ethylene (both fresh and from recycle stream 1104) to produce more propylene.

Using the disclosed systems, the metathesis process is improved because a greater amount of propylene product can be formed with the same amount of an initial isobutylene feed, the lifetime of the metathesis catalyst is increased, and the recycling process for the streams exiting the metathesis and skeletal isomerization processes is more efficient. This leads to a more cost-effective metathesis process for generating greater amounts of propylene.

Example

The following example is included to demonstrate embodiments of the appended claims using the above described system and methods of treating C4+ streams exiting metathesis and skeletal isomerization processes. The example is intended to be illustrative, and not to unduly limit the scope of the appended claims. Those of skill in the art should appreciate that many changes can be made in the specific embodiments which are disclosed and still obtain a like or similar result without departing from the spirit and scope of the disclosure herein. In no way should the following examples be read to limit, or to define, the scope of the appended claims.

Propylene formation was evaluated using a metathesis system with the hydroisomerization/hydrogenation reactions in a hydrotreater and flow pathway per the embodiment in the FIGURE, and a second metathesis system without the hydroisomerization/hydrogenation reactions. The metathesis process and skeletal isomerization process is the same for both systems. The C4+ treatment process for the two systems varies only in the presence of the hydroisomerization/hydrogenation reactions.

The metathesis system without the hydroisomerization/hydrogenation reactions has the same flow pathways for combining the streams containing the co-produced 1-butene, 2-butene, butadiene, and heavy olefins-containing before separating the C5+ heavy olefins from the combined streams in a gasoline distillation tower. The combined stream simply does not undergo hydroisomerization/hydrogenation reactions after being distilled in the gasoline distillation tower.

Operating conditions for metathesis process: The metathesis process in both systems had a metathesis reactor, a de-ethanizer, and a de-propanizer. The operating conditions for the metathesis reactor in both systems were a temperature of 600° F. and a pressure of 450 psig. The metathesis catalyst was $WO_3$ on $SiO_2$.

The operating conditions for the de-ethanizer tower in both systems were a temperature of −1° F. at the top of the tower and 180° F. at the bottom of the tower. The pressure was 400 psig, and there were 30 ideal stages for the distillation.

The operating conditions for the de-propanizer tower in both systems were a temperature of 110° F. at the top of the tower and 230° F. at the bottom of the tower. The pressure was 260 psig, and there were 40 ideal stages for the distillation.

Operating conditions for skeletal isomerization process: The skeletal isomerization process in both systems had a skeletal isomerization reactor and butene distillation tower. The operating conditions for the skeletal isomerization reactor in both systems were a temperature of 750° F. and a pressure of 10 psig. The isomerization catalyst was commercially available ferrierite.

The operating conditions for the butene distillation tower in both systems were a temperature of 135° F. at the top of the tower and 280° F. at the bottom of the tower. The pressure was 115 psig, and there were 50 ideal stages for the distillation.

The C2-C3 stream exiting the top of the butene distillation tower was combined with the metathesis product stream via pathway 1203 in both systems. This allowed for the separation and recovery of additional C3 and well as more ethylene for recycle stream 1104.

Operating conditions for C4+ treatment process: The operating conditions for the gasoline distillation tower in both systems were a temperature of 130° F. at the top of the tower and 260° F. at the bottom of the tower. The pressure was 115 psig. This gasoline distillation tower utilized 20 ideal stages for the distillation.

For the system using the hydroisomerization hydrotreater, the operating conditions of the hydrotreater were a temperature of 150° F. and a pressure of 400 psig. The hydroisomerization catalyst was a commercially available Pd on an alumina support catalyst.

Results: Mass balance data for both systems, in their steady state, were prepared. Though their products streams are combined, the metathesis and skeletal isomerization processes are run separately. Thus, the mass balance for the skeletal isomerization process is the same for both systems. The mass balance for this process with references to the streams in the FIGURE are shown in Table 1.

TABLE 1

Mass balance for the Skeletal Isomerization Process

| Component | Fresh Isobutylene feed for SI (lb/hr) (Stream 1201) | SI Reactor Prod. (lb/hr) (Stream 1202) | Liq. Overhead Recycle Prod. from Butene tower (lb/hr) (Stream 1205) | Bottom Prod. from Butene tower (lb/hr) (Stream 1206) |
|---|---|---|---|---|
| ethylene | | 527 | * | |
| propylene | | 5006 | * | |
| 1-butene | | 23497 | 11749 | 11748 |
| Cis-2-butene | | 26228 | | 26228 |
| Trans-2-butene | | 53269 | | 53269 |
| isobutylene | 110000 | 117766 | 117766 | |
| butadiene | | 7 | | 7 |
| 1-pentene | | | | |
| cis-2-pentene | | | | |
| trans-2-pentene | | | | |

TABLE 1-continued

Mass balance for the Skeletal Isomerization Process

| Component | Fresh Isobutylene feed for SI (lb/hr) (Stream 1201) | SI Reactor Prod. (lb/hr) (Stream 1202) | Liq. Overhead Recycle Prod. from Butene tower (lb/hr) (Stream 1205) | Bottom Prod. from Butene tower (lb/hr) (Stream 1206) |
|---|---|---|---|---|
| 2-methyl-2-butene | | 13222 | | 13222 |
| C6+ | | | | |
| Total | 110000 | 239522 | 129515 | 104474 |

SI = skeletal isomerization
Prod. = product
Liq. = liquid
*ethylene and propylene vapors were removed from the SI reactor product stream in the butene distillation tower via pathway 1203 in FIGURE and recovered by the de-ethanizer and de-propanizer.

The stream 1202 exiting the SI reactor, denoted as "SI reactor product" in Table 1, is mostly unreacted isobutylene and linear olefins. This stream is fed to the butene distillation tower to separate out isobutylene for recycling back to the skeletal isomerization reactor. This recycle stream 1205, denoted "Liquid Overhead Recycle Product from Butene tower" in Table 1, is mainly unreacted isobutylene and about half of the produced 1-butene. The C2 and C3 compounds produced during the isomerization reaction are also separated out by the butene distillation tower and removed as vapor via pathway 1203 in the FIGURE. The remaining C4+ compounds in the SI product stream are removed from the bottom of the butene tower in stream 1206, denoted "Bottom Product from Butene tower" in Table 1. This product stream is combined with a metathesis product stream in the C4+ treatment process, while the C2-C3 vapor stream is further separated by the de-ethanizer and de-propanizer in the metathesis process.

Table 2 displays the mass balance for a metathesis system without a hydrotreater process used for treating the co-produced butenes and heavy olefins exiting both the metathesis and skeletal isomerization reactors. Table 3 displays the mass balance for a metathesis system with the hydrotreater process, according to the FIGURE.

TABLE 2

Mass balance for a metathesis system without hydroisomerization

| Component | Ethylene feed for Met. (lb/hr) | Met. feed (lb/hr) | Met prod. (lb/hr) | SI Bottom Prod. from Butene tower (lb/hr) | Gasoline prod. (lb/hr) | propylene prod. (lb/hr) |
|---|---|---|---|---|---|---|
| ethylene | 33023 | 120527 | 86977 | 0 | | |
| propylene | | | 109953 | 0 | | 114959‡ |
| 1-butene | | 56430 | 44682 | 11748 | | |
| Cis-2-butene | | 35408 | 9179 | 26228 | | |
| Trans-2-butene | | 65446 | 12172 | 53269 | | |
| butadiene | | 7 | | 7 | | |
| 1-pentene | | | 1871 | | 1871 | |
| cis-2-pentene | | | 3734 | | 3734 | |

TABLE 2-continued

Mass balance for a metathesis system without hydroisomerization

| Component | Ethylene feed for Met. (lb/hr) | Met. feed (lb/hr) | Met prod. (lb/hr) | SI Bottom Prod. from Butene tower (lb/hr) | Gasoline prod. (lb/hr) | propylene prod. (lb/hr) |
|---|---|---|---|---|---|---|
| trans-2-pentene | | | 8259 | | 8259 | |
| 2-methyl-2-butene | | | | 13222 | 13222 | |
| C6+ | | | 982 | | 982 | |
| Total | 33023 | 277818 | 277809 | 104474 | 28068 | 114959‡ |

Met. = metathesis
SI = skeletal isomerization
Prod. = product
‡ = includes the 5006 lb/hr of propylene produced in the SI Reactor.

The metathesis feed in Table 2 has a large amount of 1-butene from both the metathesis product stream and the skeletal isomerization product stream. The 1-butene does not react with ethylene to form propylene. Instead, the 1-butene reacts in the metathesis reactor to form heavy (C5+) olefins, which will increase the yield of gasoline, which is an undesirable side product.

Adding the hydroisomerization reaction to the metathesis system decreases the 1-butene and increases of 2-butene. This results in an increase in propylene formation, as shown in Table 3. It also reduces the amount of gasoline by-product produced in the metathesis reaction. The hydrotreater system in the FIGURE was also able to reduce the amount of C4 diolefins such as BD by about 90% as shown in Table 3.

the hydrotreater, the amount of 1-butene that is recycled to the metathesis reactor decreased by about 97% while the amount of cis-2-butene and trans-2-butene increase by 31% and 26%, respectively. This increase in the amount of 2-butenes has led to about 22% more propylene produced than the system without the hydrotreater. Table 4 displays these differences between the two systems.

TABLE 4

Comparison of Metathesis feed

| Component | Met. feed without hydrotreater (lb/hr) | Met. feed with hydrotreater (lb/hr) | Difference |
|---|---|---|---|
| 1-butene | 56430 | 1266 | 97% reduction |
| Cis-2-butene | 35408 | 46269 | 31% increase |
| Trans-2-butene | 65446 | 82468 | 26% increase |
| Butadiene | 7 | 1 | 86% reduction |

Further, the decrease in 1-butenes in the metathesis feed reduces the side reactions that produce the C5+ olefins, as shown by the 50% reduction in the gasoline yield in Table 3 (13,699 lb/hr) versus Table 2 (28,068 lb/hr).

The presently disclosed metathesis system with the hydroisomerization/hydrogenation reaction not only increases the amount of propylene produced using the same initial amount of isobutylene, but it also reduces the C4 diolefins (BD) and 1-butene that would otherwise increase the yield of gasoline byproduct. Reduction and/or removal

TABLE 3

Mass balance for a metathesis system with hydroisomerization

| Component | Ethylene feed for Met. (lb/hr) (Stream 1101) | Met. feed (lb/hr) (Streams 1104/1303) | Met prod. (lb/hr) (Stream 1103) | SI Bottom Prod. from Butene tower (lb/hr) (Stream 1206) | Gasoline Tower feed (lb/hr) (Streams 1106/1206) | Gasoline prod. (lb/hr) (Stream 1302) | Hydro. prod. (lb/hr) (Stream 1303) | Propylene prod. (lb/hr) (Stream 1107) |
|---|---|---|---|---|---|---|---|---|
| ethylene | 44729$^a$ | 120527 | 75271 | 0 | | | | |
| propylene | | | 136054 | 0 | | | | 141059‡ |
| 1-butene | | 1266 | 913 | 11748 | 12661 | | 1266 | |
| Cis-2-butene | | 46269 | 16281 | 26228 | 42508 | | 46269 | |
| Trans-2-butene | | 82468 | 21563 | 53269 | 74832 | | 82472 | |
| butadiene | | 1 | 0 | 7 | 7 | | 1 | |
| 1-pentene | | | 55 | | 55 | 55 | | |
| cis-2-pentene | | | 110 | | 110 | 110 | | |
| trans-2-pentene | | | 242 | | 242 | 242 | | |
| 2-methyl-2-butene | | | | 13222 | 13221 | 13221 | | |
| C6+ | | | 41 | | 41 | 41 | | |
| Total | 44729 | 250531 | 250530 | 104474 | 143677 | 13669 | 130008 | 141059 |

Met. = metathesis
SI = skeletal isomerization
Hydro. = hydrotreater
Prod. = product
$^a$ = the amount of ethylene is increased to accommodate in the increase in 2-butene in the metathesis feed.
‡ = includes the 5006 lb/hr of propylene produced in the SI reactor.

As shown in Table 3, the gasoline fractionation tower removes the C5+ compounds before they reach the hydrotreater. This allows the hydrotreater to reduce the C4 diolefins by about 90% which enables the hydrotreater to convert about 90% of the 1-butene to 2-butene. By adding of the diolefins from the metathesis recycle stream further results in an increase in metathesis catalyst lifetime. Thus, the presently disclosed metathesis system is able to utilize isobutylene for the increased production of propylene and increased lifetime of the metathesis catalyst.

The following are incorporated by reference in their entirety: U.S. Pat. Nos. 7,074,976 and 6,872,862.

The invention claimed is:

1. A method of producing propylene comprising
   a) combining a $C_4+$ olefin product stream from a skeletal isomerization unit and a $C_4+$ olefin product stream from a metathesis unit;
   b) introducing the combined streams into a gasoline fractionation tower;
   c) separating the combined streams in said gasoline fractionation tower to form a $C_5+$ olefin stream and a gasoline fractionation distillate comprising $C_4$ olefins;
   d) transferring the gasoline fractionation distillate to a hydroisomerization hydrotreater reactor;
   e) converting $C_4$ diolefins in the gasoline fractionation distillate to $C_4$ mono-olefins in said hydroisomerization hydrotreater reactor;
   f) converting 1-butene in the gasoline fractionation distillate to 2-butene in said hydroisomerization hydrotreater reactor to form a 2-butene-rich olefin product stream;
   g) de-oxygenating said 2-butene-rich olefin product stream to form a treated 2-butene rich stream;
   h) co-feeding the treated 2-butene rich stream with at least one ethylene stream into the metathesis unit; and,
   i) producing propylene.

2. The method of claim 1, wherein both $C_4+$ olefin product streams comprise 1-butene, 2-butene, butadiene, and $C_5+$ diolefins and mono-olefins.

3. The method of claim 1, wherein converting step f) converts at least 80% of said 1-butene to 2-butene.

4. The method of claim 1, wherein the hydroisomerization hydrotreater reactor contains Pd, Pt, Ru or Cu on silica, alumina or silica alumina as a catalyst.

5. The method of claim 1, wherein the catalyst in the hydroisomerization hydrotreater reactor is palladium on an alumina support.

6. The method of claim 1, wherein the yield of propylene is at least 10% greater than the yield of methods that do not have steps a-f.

7. The method of claim 1, wherein the lifetime of the catalyst in the metathesis unit is 10% or more longer than methods that do not have steps a-f.

8. A system for producing propylene comprising:
   a) a skeletal isomerization unit comprising:
      i) a skeletal isomerization reactor having an inlet for receiving at least an isobutylene feed stream and an outlet for release of a skeletal isomerization reactor stream;
      ii) a butene distillation column fluidly connected to the outlet of said skeletal isomerization reactor, said butene distillation column having a first outlet for release of a $C_2$-$C_3$ olefin vapor stream, a second outlet for release of a recycle stream comprising isobutylene and a first portion of 1-butene, and a third outlet for release of a skeletal isomerization product stream comprising 2-butene, a second portion of 1-butene, butadiene and $C_5+$ olefins, wherein said recycle stream is introduced into said skeletal isomerization reactor by said inlet;
   b) a metathesis unit comprising:
      i) a metathesis reactor having a first inlet for receiving at least an ethylene feed stream, a second inlet for receiving a $C_4$ olefin feed stream, and outlet for releasing a metathesis product stream, wherein said metathesis product stream comprises ethylene, propylene, and $C_4+$ hydrocarbons;
      ii) a de-ethanizer unit having an inlet fluidly connected to the metathesis reactor for receiving said metathesis product stream, said de-ethanizer having a top outlet for a recycle ethylene stream that can be combined with said ethylene feed stream and a bottom outlet for release of a de-ethanized stream;
      iii) a de-propanizer unit having an inlet fluidly connected to the de-ethanizer unit for receiving said de-ethanized stream, said de-propanizer having a top outlet for a stream of produced propylene and a bottom outlet for release of an untreated metathesis stream comprising $C_4+$ hydrocarbons;
   c) a hydroisomerization unit comprising:
      i) a gasoline fractionation tower having an inlet for receiving and combining the untreated metathesis stream and the skeletal isomerization product stream, wherein said gasoline distillation tower separates the combined streams into a $C_5+$ olefin stream and a $C_4$ stream;
      ii) a hydroisomerization reactor having an inlet for receiving the $C_4$ stream from the gasoline fractionation tower, and an outlet for a 2-butene rich $C_4$ olefin stream, wherein said hydroisomerization reactor converts diolefins to mono-olefins and isomerizes 1-butene to 2-butene;
      iii) a first line exiting the bottom of said gasoline fractionation tower for carrying the $C_5+$ olefin stream to a refinery for gasoline blending;
      iv) a second line exiting the top of said hydroisomerization reactor for carrying the 2-butene rich $C_4$ olefin stream to a de-oxygenation unit; and
      v) a third line exiting the de-oxygenation unit for carrying the de-oxygenated 2-butene rich $C_4$ olefin stream to the second inlet of said metathesis reactor.

9. The system of claim 8, further comprising a line fluidly connecting the first outlet of said butene distillation column to the inlet of said de-ethanizer such that said $C_2$-$C_3$ olefin vapor stream undergoes separation in the de-ethanizer and said de-propanizer.

10. The system of claim 8, further comprising a recycle line for carrying said $C_2$-$C_3$ olefin vapor stream to said skeletal isomerization reactor.

11. The system of claim 8, wherein the de-oxygenation unit removes water, oxygen, and oxygenates from the 2-butene rich $C_4$ olefin stream.

12. The system of claim 8, wherein the hydroisomerization reactor has a catalyst having one or more of Pd, Pt, Ru, Cu on a silica, alumina or silica/alumina support.

13. The system of claim 12, wherein the catalyst in the hydroisomerization reactor unit is palladium on an alumina support.

14. A method for producing propylene comprising:
   a) producing a first $C_4+$ olefin product stream in a skeletal isomerization unit comprising
      i) isomerizing an isobutylene feed stream in a skeletal isomerization reactor;
      ii) separating, in a butene distillation column, the isomerized feed stream into a $C_2$-$C_3$ olefin vapor stream, a recycle stream comprising isobutylene and a first portion of 1-butene, and the first $C_4+$ olefin stream;
   b) producing a second $C_4+$ olefin product stream in a metathesis reactor unit comprising
      i) reacting at least one ethylene stream and a 2-butene rich stream in a metathesis reactor to form a metathesis product stream comprising $C_2+$ olefins;

ii) separating, in a de-ethanizer unit, ethylene from the metathesis product stream;

iii) separating, in a de-propanizer unit, propylene from the metathesis product stream to form the second $C_4+$ olefin stream and a propylene product stream;

c) producing a 2-butene rich stream in a hydroisomerization unit comprising i) combining the first and second $C_4+$ olefin stream in a gasoline fractionation tower;

ii) separating, in said gasoline fractionation tower, $C_5+$ olefins from a $C_4$ olefin distillate;

iii) introducing the $C_4$ olefin distillate into a hydroisomerization hydrotreatment reactor;

iv) converting diolefins in the $C_4$ olefin distillate to mono-olefins, then converting 1-butene in the $C_4$ olefin distillate to 2-butene to form the 2-butene rich stream; and, d) feeding said 2-butene rich stream into said metathesis reactor to produce propylene.

15. The method of claim 14, wherein said 2-butene rich stream is treated to remove oxygen-containing compounds before being fed into said metathesis reactor.

16. The method of claim 14, further comprising combining said $C_2$-$C_3$ olefin vapor stream with said metathesis product stream before step bii).

17. The method of claim 14, further comprising recycling said $C_2$-$C_3$ olefin vapor stream into said skeletal isomerization reactor.

18. The method of claim 14, wherein the yield of propylene is at least 10% greater than the yield of systems that do not have step c.

19. The method of claim 14, wherein the lifetime of the catalyst in the metathesis unit is 10% or more longer than systems that do not have step c.

* * * * *